United States Patent [19]

Bhupathy et al.

[11] Patent Number: 5,614,632
[45] Date of Patent: Mar. 25, 1997

[54] PROCESS FOR THE PREPARATION OF LEUKOTRIENE ANATGONISTS

[75] Inventors: Mahadevan Bhupathy, Edison; James M. McNamara, Rahway, both of N.J.; Daniel R. Sidler, Mansfield, Pa.; Ralph P. Volante, Cranbury; James Bergan, Rahway, both of N.J.

[73] Assignee: Merck & Co., Inc., Rahway, N.J.

[21] Appl. No.: 439,733

[22] Filed: May 12, 1995

Related U.S. Application Data

[60] Division of Ser. No. 350,428, Dec. 9, 1994, which is a continuation-in-part of Ser. No. 174,931, Dec. 28, 1993, abandoned.

[51] Int. Cl.$^6$ .................................................. C07D 215/18
[52] U.S. Cl. ............................................................ 546/180
[58] Field of Search ............................................. 546/180

[56] References Cited

U.S. PATENT DOCUMENTS 5,270,234  12/1993  Zamboni et al. ................. 437/44
5,428,033   6/1995  Belley ............................... 514/228.2

FOREIGN PATENT DOCUMENTS 480717  4/1992  European Pat. Off. .

OTHER PUBLICATIONS

King, et al, J. Org. Chem. 1993, 58:3731–3735.

Primary Examiner—C. Warren Ivy
Assistant Examiner—D. Margaret M. Mach
Attorney, Agent, or Firm—Mollie M. Yang; David L. Rose

[57] ABSTRACT

The present invention relates to a process for the preparation of a compound of formula (I) or a sodium salt thereof

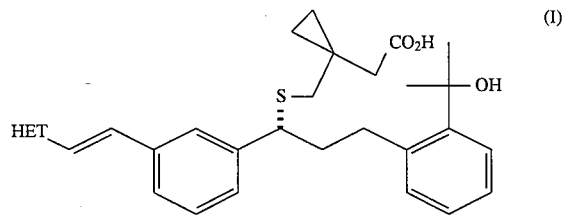

(I)

wherein HET is 7-chloroquinolin-2-yl or 6,7-difluoroquinolin-2-yl, which comprises: reacting the dilithium dianion of 1-(mercaptomethyl)cyclopropaneacetic acid with a compound of formula (II)

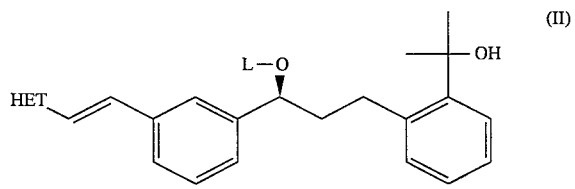

(II)

wherein HET is as defined above and L is arylsulfonyl or alkylsulfonyl. The invention further provides the dicyclohexylamine salt of a compound of formula (I).

7 Claims, 6 Drawing Sheets

PROCESS FOR THE PREPARATION OF LEUKOTRIENE ANATGONISTS

CROSS REFERENCE

This is a division of application Ser. No. 08/350,428 filed Dec. 9, 1994 which is application is a continuation-in-part of U.S. Ser. No. 08/174,931 filed Dec. 28, 1993, now abandoned, which is hereby incorporated in its entirety.

BACKGROUND OF THE INVENTION

The leukotrienes constitute a group of locally acting hormones, produced in living systems from arachidonic acid. The major leukotrienes are Leukotriene B4 (abbreviated as LTB4), LTC4, LTD4, and LTE4. The biosynthesis of these leukotrienes begins with the action of the enzyme 5-lipoxygenase on arachidonic acid to produce the epoxide known as Leukotriene A4 (LTA4), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various disease states are also discussed in the book by Rokach.

Recently a number of compounds of formula (1) in which A represents optionally substituted heterocycle, and pharmaceutically acceptable salts thereof, have been disclosed as leukotriene antagonists and inhibitors of leukotriene biosynthesis.

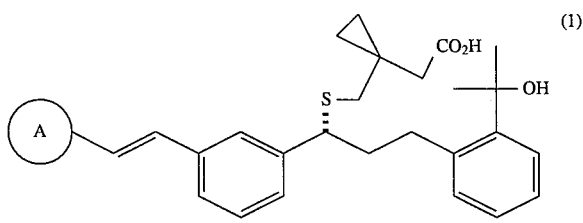

(1)

EP 480,717 discloses compounds of formula (1) in which A represents optionally substituted quinoline; more specifically disclosed is the compound in which A represents 7-chloro-2-quinolinyl. U.S. Pat. No. 5,270,324 discloses two compounds of formula (1) in which A represents 6-fluoro- or 6,7-difluoro-2-quinolinyl. In co-pending is application U.S. Ser. No. 994,869, filed Dec. 22, 1992 (EP Published Application 604,114) there is disclosed compounds in which A is halo-substituted thieno[2,3-b]pyridine, particularly 2,3-dichlorothieno[2,3-b]pyridin-5-yl.

The reported syntheses of compounds of formula (1) proceed through their corresponding methyl esters and involve coupling methyl 1-(mercaptomethyl)cyclopropaneacetate with a mesylate exemplified by formula (III), generated in situ. The methyl esters of compounds of formula (I) are hydrolyzed to the free acids and the latter converted directly to the corresponding sodium salts. This process is not particularly suitable for large-scale production because it requires tedious chromatographic purification of the methyl ester intermediates and/or the final products, and the product yields are low. Furthermore, the final products, as the sodium salts, were obtained as amorphous solids which are often not ideal for pharmaceutical formulation.

Accordingly, there exists the need for an efficient synthesis of compounds of formula (1) which is amenable to scale-up, provides improved overall product yield, and provides the product sodium salts in crystalline form.

King et al, *J. Org. Chem.*, 1993, 58:3731–3735 reported the synthesis of L-699,392 via the following sequence:

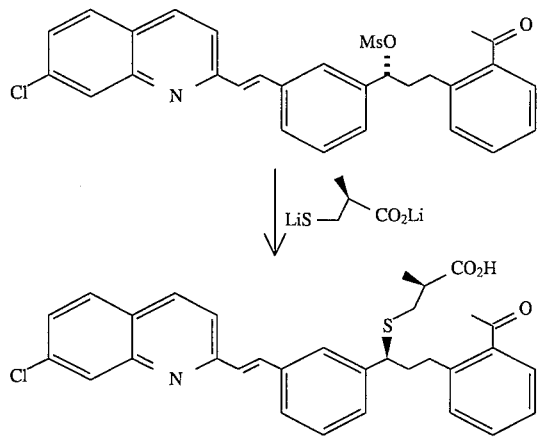

SUMMARY OF THE INVENTION

The present invention relates to an improved process for the preparation of compounds of formula (I); to an improved process for the preparation of the precursor 1-(mercaptomethyl)cyclopropane-acetic acid; and to intermediate compounds.

Compounds of formula (I) are leukotriene antagonists and are useful agents in the treatment of asthma as well as other conditions mediated by leukotrienes, such as inflammation and allergies.

DETAILED DESCRIPTION OF THE INVENTION

Figure 1:
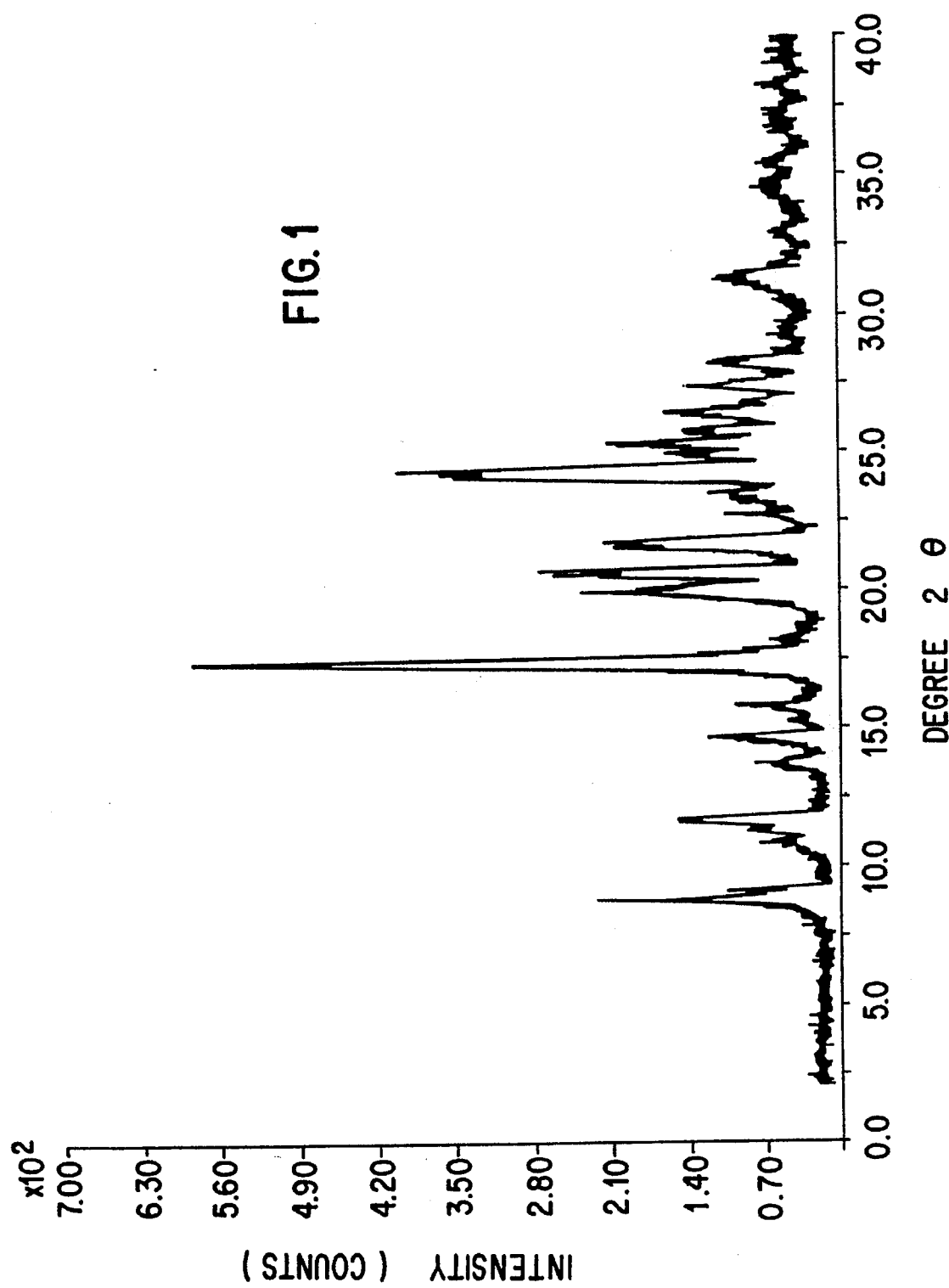
FIG. 1 depicts the X-ray powder diffraction pattern of the compound of Example 6.

The present invention provides in one aspect a process for the preparation of a compound of formula (I) or a sodium salt thereof

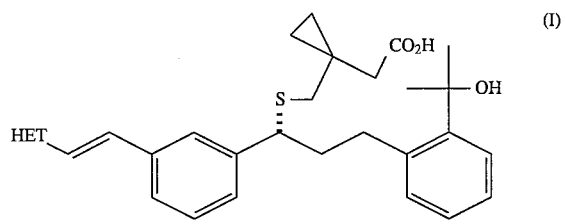

(I)

wherein HET is 7-chloroquinolin-2-yl or 6,7-difluoroquinolin-2-yl, which comprises: generating the dilithium dianion of 1-(mercaptomethyl)cyclopropaneacetic acid; reacting said dianion with a compound of formula (II)

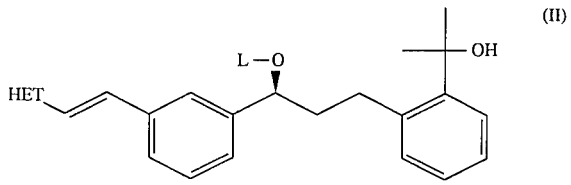

wherein HET is as defined previously and L is arylsulfonyl or alkylsulfonyl. Preferably, HET is 7-chloroquinolin-2-yl, and L is methanesulfonyl. In a preferred embodiment, the process further comprises: converting a compound of formula (I) into the dicyclohexylamine salt; and converting the dicyclohexylamine salt of a compound of formula (I) into the corresponding sodium salt.

The present invention provides in another aspect the dicyclohexylamine salt of a compound of formula (I). The dicyclohexylamine salt is readily isolable in crystalline form and is advantageously used as a means for the purification of a compound of formula (I), and in the preparation of crystalline sodium salt of a compound of formula (I).

Accordingly, another aspect of the invention provides a process for the preparation of crystalline sodium salt of a compound of formula (I) which comprises: treating the dicyclohexylamine salt of a compound formula (I) with an acid; treating the product thus obtained with a source of sodium ion; crystallizing the sodium salt of a compound of formula (I). In a preferred embodiment, said acid is acetic acid, and said crystallization is effected from toluene/acetonitrile.

The invention also provides the compound 1-(mercaptomethyl)cyclopropaneacetic acid, and salts thereof, preferably the dilithium salt. In yet another aspect of the invention there is provided a process for the preparation of 1-(mercaptomethyl)cyclopropaneacetic acid which comprises: providing a solution of 1-(acetylthiomethyl)cyclopropaneacetonitrile in an organic solvent; treating said solution with an aqueous solution of a base to form a biphasic phase. In a preferred embodiment, said base is sodium hydroxide.

Yet another aspect of the invention provides crystalline methanesulfonates of the formula (III)

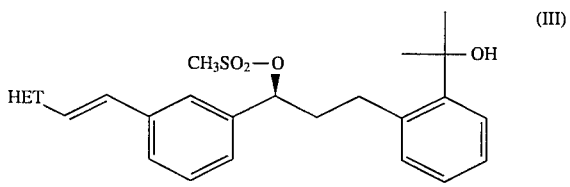

wherein HET is as previously defined under formula (I).

DEFINITIONS

AcS=acetylthio
DCHA=dicyclohexylamine
DMF=dimethylformamide
DSC=differential scanning calorimetry
HOAc=acetic acid
IPAc=isopropyl acetate
MsCl=methanesulfonyl chloride=mesyl chloride
RT=room temperature
THF=tetrahydrofuran "Arylsulfonyl" means any benzenesulfonyl groups commonly used to convert hydroxy to a leaving group, and includes substituted benzenesulfonyl such as toluenesulfonyl.

"Alkylsulfonyl" means lower alkanesulfonyl having one to four carbon atoms such as methanesulfonyl.

Before describing the invention in detail, the overall reaction sequence in the synthesis of compounds of formula (I) is first briefly discussed. The reaction sequence starting from known materials is illustrated in Schemes 1 to 3.

SCHEME 1

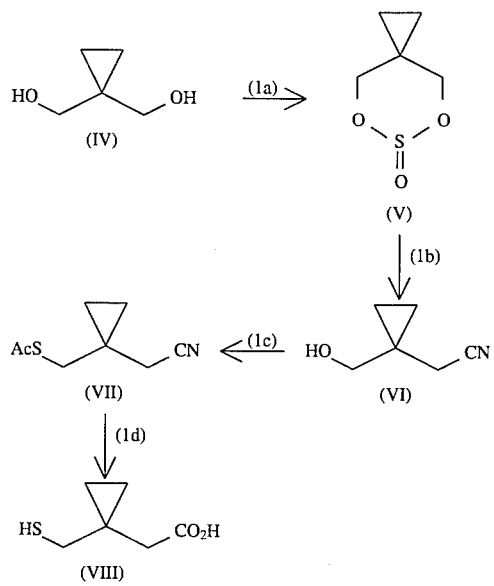

Scheme 1 depicts the preparation of the thiomethylcyclopropaneacetic acid sidechain precursor. In step (1a), 1,1-cyclopropanedimethanol (IV) is converted to the corresponding cyclic sulfite (V) using thionyl chloride and in the presence of a base such as diisopropylethylamine. The reaction is carried out in an inert organic solvent, for example halogenated hydrocarbon such as dichloromethane, or aromatic hydrocarbon such as toluene. The reaction is essentially complete by the end of addition of thionyl chloride.

In step (1b), the cyclic sulfite (V) is treated with a catalytic amount of sodium iodide and sodium cyanide to provide the corresponding hydroxy-nitrile (VI). The reaction is carried out in dimethylformamide/toluene or dimethylformamide/isopropyl acetate at a temperature ranging from about 65° to about 90° C. Preferably the reaction temperature is at about 70° C.

In step (1c), the hydroxy-nitrile (VI) is first converted to its mesylate using methanesulfonyl chloride and in the presence of a tertiary amine base such as diisopropylethylamine, triethylamine, and the like. The mesylate is then treated with potassium thioacetate to provide 1-(acetylthiomethyl)cyclopropaneacetonitrile (VII). Alternatively, the mesylate is treated with thiolacetic acid in the presence of a base such as triethylamine to provide (VII)

In step (1d), 1-(acetylthiomethyl)cyclopropaneacetonitrile (VII) is converted to 1-(mercaptomethyl)cyclopropaneacetic acid (VIII) in a biphasic solvent system. This step is described in further detail later in the specification.

The reaction sequence of Scheme 1 may also be carried out according to the following procedure.

The conversion to the cyclic sulfite (V) may be accomplished by reacting the diol (IV) with diisopropylsulfite, [$(CH_3)_2CH$]$_2SO_3$, which in turn is obtained from thionyl chloride and isopropanol. The reaction of the diol and diisopropylsulfite is carried out in an inert organic solvent such as dimethylformamide/toluene, and in the presence of a catalytic amount of a base such as sodium t-butoxide. The reaction solution preferably is dried (to KF<100 μg/mL) prior to addition of the base. Isopropanol produced in the reaction is removed by distillation to drive the reaction to product formation. Sodium cyanide and catalytic sodium iodide are added to the cyclic sulfite solution, and the reaction is carried out at elevated temperature, e.g. at about 70° C., to provide the hydroxy-nitrile compound (VI). The sodium cyanide and sodium iodide are preferably dried prior to use.

The hydroxy-nitrile (VI) in toluene/DMF is convened to the corresponding mesylate as described above. The ratio of toluene:DMF for the mesylation is preferably in excess of 1.9:1; typically, the ratio used is about 2.1–2.4:1. Displacement of the mesyl group with thiolacetic acid in the presence of a base such as triethylamine provides the compound (VII), which is then hydrolyzed as described later to provide the thiol acid (VIII).

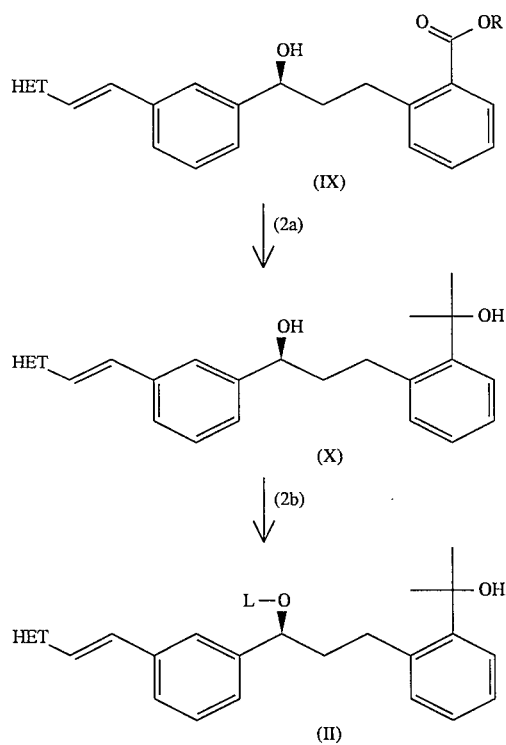

Scheme 2 depicts the preparation of the "backbone" portion of compounds of formula (I). In Scheme 2, R is a lower alkyl group such as methyl and ethyl; L is arylsulfonyl or alkylsulfonyl, for example, toluenesulfonyl or methanesulfonyl. Preferably, R is methyl and L is methanesulfonyl. In step (2a) the hydroxy ester (IX) is converted to the diol (X) using a Grignard reagent such as methyl magnesium chloride and in the presence of cerium chloride. The molar ratio of cerium chloride to methyl magnesium chloride (CeCl$_3$:CH$_3$MgCl) may be from about 1:1 to about 1:5, and is preferably about 1:4 to about 1:5; the molar ratio of the hydroxy ester (IX) and cerium chloride may range from about 1:0.25 to about 1:1, and preferably in the range of about 1:0.5 to about 1:1. The reaction is carried out under anhydrous conditions, preferably using pre-dried cerium chloride, the hydroxy ester (IX), and solvents. The reaction is carried out in inert organic solvent such as THF/toluene at temperature in the range of about –5 to about 5° C. The reaction solution containing the diol (X) may be concentrated and used in the next step, or the diol (X) may be crystallized from an aromatic solvent such as toluene, and a hydrocarbon solvent such as hexane or heptane, in a ratio of about 1:1 to about 1:3.

In step (2b) methanesulfonyl chloride is used to convert the diol (X) into the mesylate (II). This reaction is described in more detailed later in the specification.

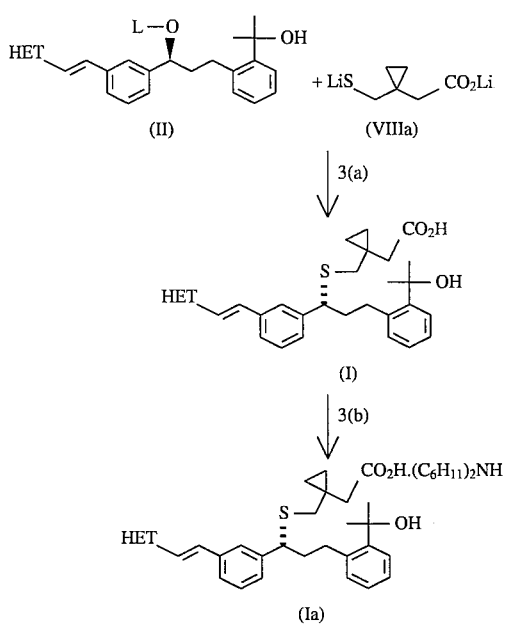

Scheme 3 depicts one aspect of the present invention relating to an improved process for the preparation of a compound of formula (I). In step 3(a) dilithium salt of 1-(mercaptomethyl)cyclopropaneacetic acid (VIIIa) is coupled with a sulfonate of formula (II). Thus 1-(mercaptomethyl)cyclopropaneacetic acid (VIII) is first converted into the dilithium dianion by contacting the former with a lithium base such as n-butyl lithium in hexane or heptane, and the like. The reaction is carried out in an inert organic solvent such as THF, toluene or a mixture thereof, and at a temperature of below 0° C., typically at about –5° C. or lower.

The sulfonate (II) is then added to the solution of the dilithium dianion. The sulfonate may be added directly as a solid, or in s solution in an inert organic solvent such as THF or toluene, preferably THF. Since the sulfonate (II) has limited stability in solution, the sulfonate solution is preferably prepared just prior to addition to the dianion solution, and in any case is best used within about 30 minutes.

The reaction mixture is maintained at below about 0° C, generally at about –5° C. until completion of the reaction, typically the reaction is complete within about 10 hours. The reaction solution containing the desired product is then treated with a water soluble carboxylic acid, e.g. acetic acid, oxalic acid, tartaric acid and the like to provide the free acid form of a compound of formula (I); a preferred carboxylic acid is tartaric acid.

In a preferred embodiment, a compound of formula (I) as obtained above is converted to the dicyclohexylamine (DCHA) salt. Thus dicyclohexylamine is added to a solution of a compound of formula (I) in ethyl acetate, followed by hexanes to effect crystallization of the dicyclohexylamine salt. Preferred ratio of ethyl acetate:hexanes is about 1:1 to about 1:2. A seed of the dicyclohexylamine salt is preferably added to the ethyl acetate/hexane solution to accelerate crystal formation. The dicyclohexylamine salts crystallize as needles.

A second crystalline form of the DCHA salt of a compound of formula (I) may be obtained by crystallization from toluene/heptane. Thus, the free acid of a compound of formula (I) in an organic solvent such as THF is treated with dicyclohexylamine; toluene is then added and the solution concentrated to remove the THF. After dilution with additional toluene, heptane is added to the toluene solution. The ratio of toluene:heptane is about 2:1 to about 3:1. The crystallization may be accelerated by the addition of DCHA salt seeds previously obtained from toluene/heptane.

Figure 2:
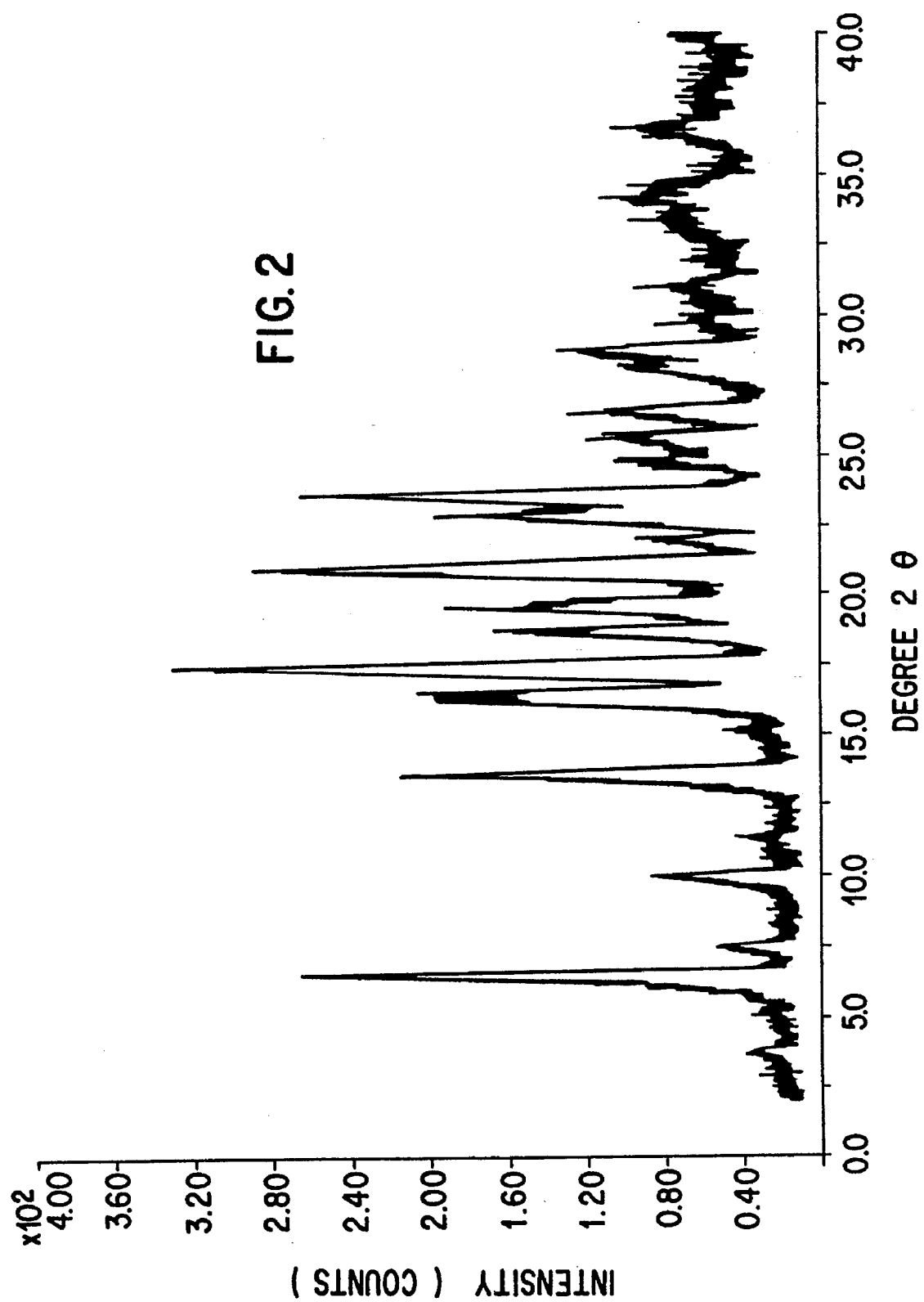
FIG. 2 depicts the X-ray powder diffraction pattern of the compound of Example 7.
Figure 6:
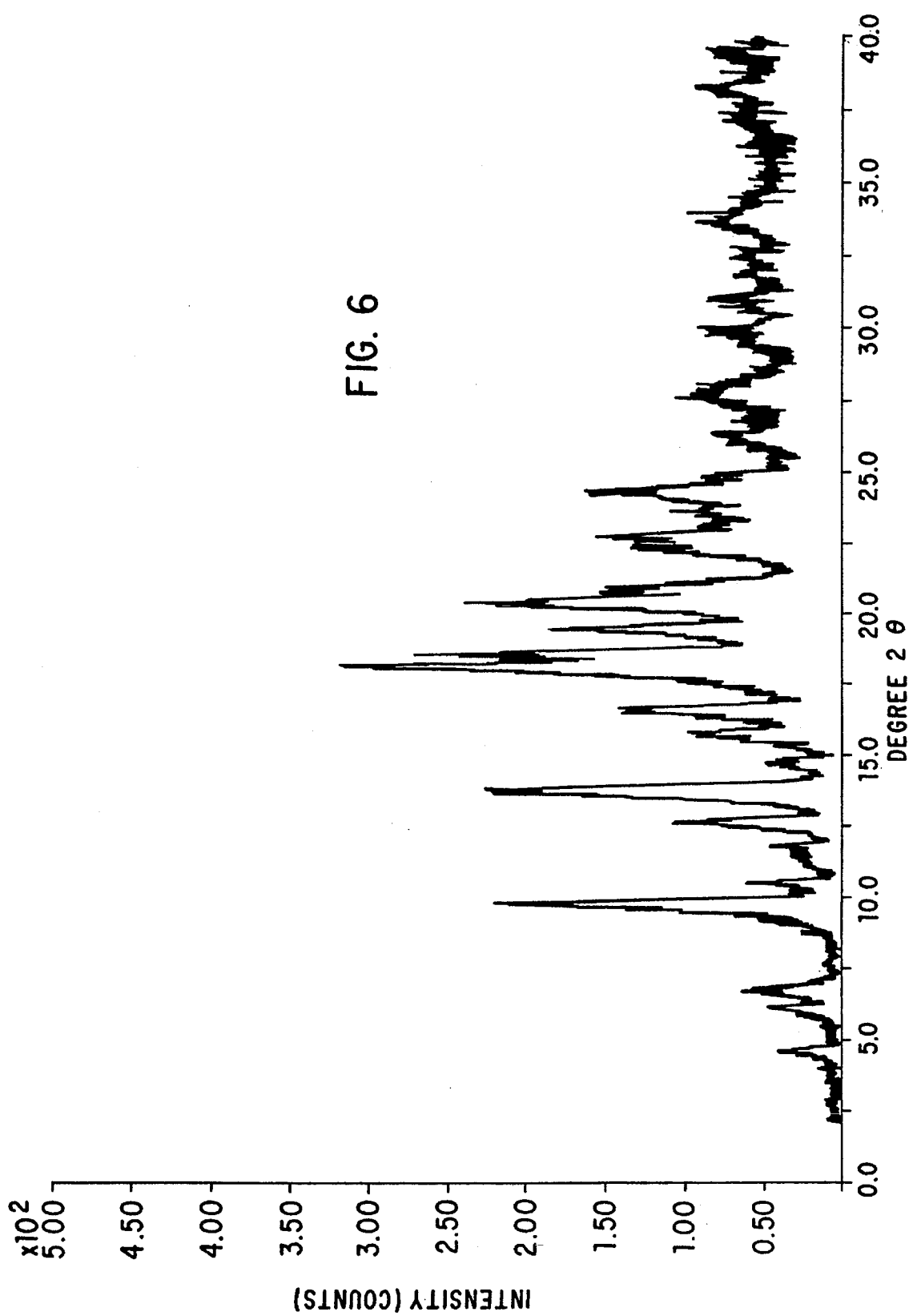
FIG. 6 depicts the X-ray powder diffraction pattern of the compound of Example 13.

The crystalline DCHA salt of a compound of formula (I) wherein HET is 7-chloroquinolin-2-yl obtained from toluene/heptane (Form B) differs from the previous form (Form A) obtained from ethyl acetate/hexanes. Form A and Form B exhibit different x-ray powder diffraction pattern as shown in FIGS. 2 and 6, respectively. Form B has been found to be the more thermodynamically stable polymorph because it has a higher melting point and is less soluble than Form A in various solvents at room temperature. The differential scanning calorimetry (DSC) curve of Form B, at a heating rate of 10°/min., shows a single melting-decomposition endotherm with an extrapolated onset temperature of approx. 139° C., a peak temperature of 143° C. and an associated heat of approx. 71 J/g. Under the same conditions, the DSC curve of Form A shows a single melting-decomposition endotherm with an extrapolated onset temperature of approx. 117° C., a peak temperature of 124° C. and an associated heat of 61 J/g. At 25° C., the solubility of Form A is 13.5±0.6 mg/ml in toluene and 7.5±0.1 mg/ml in ethyl acetate; the solubility of Form B is 18.7±0.2 mg/ml in toluene and 6.6±0.1 mg/ml in ethyl acetate The readily isolable crystalline dicyclohexylamine salt, in either form, offers a simple and efficient method for the purification of a compound of formula (I), thereby circumventing the need for tedious chromatographic purification and resulting in higher product yields.

Returning now to the various other aspects of the present invention. Another aspect of the present invention provides a process for the preparation of crystalline sodium salt of a compound of formula (I) from the corresponding dicyclohexylamine salt. Thus, the dicyclohexylamine salt (Ia) is added to a well agitated mixture of an organic solvent and water. The organic solvent may be for example an aromatic hydrocarbon, preferably toluene; an ester such as ethyl acetate; an ether such as a THF; or a mixture thereof, for example toluene/THF. To this suspension at room temperature is added a water soluble organic acid, for example acetic acid, oxalic acid, tartaric acid, and the like; acetic acid is preferably used. The organic layer containing the free acid is then treated with a source of sodium ion, for example sodium hydroxide, which is used in approximately equimolar amount with the free acid.

The solution of the sodium salt in the organic solvent is azeotropically dried under vacuum and concentrated. Acetonitrile is added at an elevated temperature of about 35° C. to about 45° C., typically at about 40° C. To accelerate crystal formation, the solution is seeded with previously formed crystals of the sodium salt. Once a good seed bed is established (within 2 hours, about 30–90 minutes at 40° C.), more acetonitrile is added to get a final ratio of acetonitrile:toluene of about 2:1 to about 9:1, preferably about 3:1.

The crystalline sodium salt of a compound of formula (I) is collected after about for 8–12 hours at 40° C.

A semi-continuous process for the crystallization of the sodium salt of a compound of formula (I) has also been developed and is described in the Examples section.

In another aspect of the invention, there is provided the novel compound 1-(mercaptomethyl)cyclopropaneacetic acid (VIII) and salts thereof, preferably the dilithium salt; and a process for the preparation thereof. Compound (VIII) is prepared from 1-(acetylthiomethyl)cyclopropaneacetonitrile (VII) by base-catalyzed hydrolysis. It has been found that hydrolysis carried out in water results in a significant amount of impurity. The amount of impurity in the reaction mixture is substantially reduced when the hydrolysis is carded out in a biphasic system containing an organic solvent and water. In the biphasic hydrolysis the desired intermediate, the thiolate of 1-(mercaptomethyl)cyclopropaneacetonitrile, is contained in the aqueous layer while neutral impurities remain in the organic layer, and are thus easily removed. In addition, crude (VII) may be used in the biphasic hydrolysis thereby avoiding the need to chromatographically purify (VII).

Thus compound (VII) is dissolved in an organic solvent; suitable solvents are for example aromatic hydrocarbons such as toluene, xylenes, and the like; the preferred solvent is toluene. A solution of compound (VII) in the organic solvent is treated with an aqueous solution of a base, such as sodium hydroxide. The reaction may be carried out at a temperature ranging from room temperature to reflux point of the reaction mixture. The hydrolysis to compound (VIII) is generally complete within several days at room temperature, typically about 6 days; and several hours at reflux.

Preferably, the biphasic mixture is maintained at room temperature until the starting material (VII) has been substantially converted to the intermediate, the sodium thiolate of 1-(mercaptomethyl)cyclopropaneacetonitrile, typically about 6 to 18 hours. The aqueous solution containing the intermediate is separated from the organic layer containing the unwanted impurities. The aqueous solution is maintained at elevated temperature up to the reflux point to complete the conversion to (VIII), e.g. at 80° C. for about 12 to 16 hours.

The solution is then acidified to form (VIII) as the free acid, and extracted with an organic solvent such as toluene or heptane, then concentrated. The concentrated solution of (VIII) in toluene is stable for several months, or compound (VIII) may be crystallized from hydrocarbon solvents such as hexanes, heptane, pentane and the like to reject some of the impurities present in the starting material (VII). Thus, a mixture of compound (VIII) in heptane is warmed to 34° C. to completely solubilize the compound, and allowed to slowly cool to about 25° C. Seeding the mixture with crystals of compound (VIII) may be used to accelerate crystal formation. The mixture is cooled to about −5° C. over about 3 hours for crystal formation.

Another aspect of the present invention provides crystalline mesylates of the formula (III):

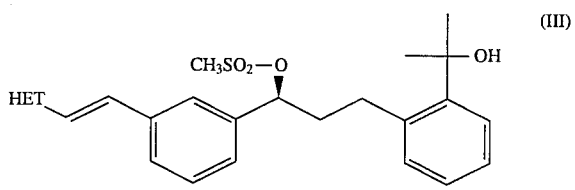

wherein HET is as previously defined under formula (I); preferably HET is 7-chloro-2-quinolinyl.

The mesylate (III) is prepared from the corresponding diol (X). The reaction is carried out in an inert organic solvent such as toluene, or toluene and acetonitrile or THF. Other suitable solvents are for example DMF or DMF/acetonitrile. The reaction is carried out in the presence of a tertiary amine base such as diisopropylethylamine, and at a temperature of ≦0° C., preferably at between about −25° C. to about −15° C. The reaction is usually complete within about 5 hrs. The preferred conditions for selective monomesylation at the secondary hydroxy are: toluene:acetonitrile solvent with a preferred ratio of about 1:2 to about 1:3; reaction temperature range of about −25° C. to about −15° C; and diisopropylethylamine as the base. The mesylate (III) has limited stability in solution; therefore, it is preferably isolated in solid form which when stored at a temperature of about −15° C. and below, is sufficiently stable for six months or more. Crystallization of the mesylate (III) is preferably carried out at temperature of 5° C. or below from toluene:acetonitrile, preferably at a ratio of about 1:2 to about 1:3. The isolation of the mesylate (III) renders the coupling with the thiolacid (VIIIa) feasible as a large-scale production process for compounds of formula (I).

The following examples are provided to more fully illustrate the present invention. The examples are not meant to limit in any manner the scope of the invention as defined in the claims.

EXAMPLE 1

1,1-Cyclopropanedimethanol Cyclic Sulfite

Method A

To a 1 L round bottom flask equipped with a stirrer, a thermocouple, a nitrogen inlet and a syringe pump were placed dichloromethane (645 mL) and 1,1-cyclopropanedimethanol ( 10.64 g; 97.93 mmol). The mixture was stirred for 10 minutes to ensure complete dissolution. N,N-Diisopropylethylamine (34.21 mL; 195.86 mmol) was added, and the solution was cooled to 0°–5° C. Thionyl chloride (7.01 mL; 96.04 mmol) was added subsurface through a teflon needle via a syringe pump over 60 minutes. The reaction solution was transferred to a separatory funnel containing cold (0°–5° C.) phosphate buffer (pH=7.2, 650 mL). After equilibration, the layers were separated. The product solution in dichloromethane was washed with 2 wt % sodium chloride solution (650 mL), and the product solution was then azeotropically dried and concentrated at 35°–40° C. under atmospheric pressure to 50 mL. Assayed yield of title compound=13.07 g (90%).

Method B

A 25 mL graduated cylinder equipped with a ground glass joint was charged with 7.14 mL (97.9 mmol) of thionyl chloride and then diluted with toluene to a volume of 21 mL.

To a 1 L round bottom flask equipped with an overhead. stirrer, a thermocouple, a nitrogen inlet and a syringe pump were placed toluene (636 mL), 1,1-cyclopropanedimethanol (10.00 g; 97.9 mmol) and N,N-diisopropylethylamine (32.41 mL; 186.1 mmol). The two phase mixture was vigorously stirred at 22° C. The thionyl chloride:toluene solution (21 mL; 97.9 mmol) was added subsurface through a teflon needle via a syringe pump over 90 minutes maintaining the reaction temperature ≦40° C. After completing the addition of thionyl chloride, the reaction mixture was stirred for another 6–12 hours to ensure max. conversion to the cyclic sulfite. The reaction mixture was transferred to a separatory funnel containing cold (0°14 5° C.) phosphate buffer (pH=7.2, 650 mL). After equilibration, the layers were separated and the product solution in toluene was washed with 2 wt % sodium chloride solution (650 mL). The product solution was then azeotropically dried and concentrated at 40–45° C./70 Torr to 70 mL. Assayed yield of title compound=12.33 g (85%).

EXAMPLE 2

1-Hydroxymethyl)cyclopropaneacetonitrile

Method A

A 250 mL round bottom flask equipped with an overhead stirrer, a thermocouple, distillation head and receiving flask was charged with the solution of the cyclic sulfite of Example 1 in dichloromethane (61 mL; 158.9 mg/,mL; 9.69 g). The solution was concentrated to approx. 20 mL by distillation under atmospheric pressure. Isopropyl acetate (2×30 mL) was added to the batch and the distillation was continued to a final volume of 13 mL. Dimethyl-formamide (21 mL) was added to the solution at >55° C. and the solution was cooled to RT.

A 250 mL round bottom flask equipped with an overhead stirrer, a thermocouple, a reflux condenser and a nitrogen inlet was charged with 40 mL of the above solution of cyclic sulfite (9.28 g; 62.6 mmol) in DMF:IPAc (4:1). Sodium cyanide (4.61 g; 94 mmol) and sodium iodide (3.75 g; 25.0 mmol) were added at RT. The reaction mixture was heated to 70°±3° C. and aged at that temperature until the reaction was complete. The reaction mixture was allowed to cool to room temperature and diluted with cold (0°–5° C.) isopropyl acetate (187 mL). The dark yellow slurry (218 mL) was transferred to a separatory funnel containing cold (0°–5° C.) 1.0M sodium hydroxide (107 mL). After equilibration, the layers were separated. The organic layer was s washed with brine (53 mL). The aqueous layer was back-extracted with cold (0°–5° C.) isopropyl acetate (107 mL), and the organic layer washed with brine (27 mL). The two organic layers were combined to provide 17.5 mg/ml of the titled compound in solution. Assayed yield of title compound=5.03 g; 72.2%.

Method B

A 12 L 3 neck round bottom flask equipped with an overhead stirrer, a thermocouple, a distillation head and 3 L receiving flask was charged with the solution of the cyclic sulfite of Example 1 in dichloromethane (2.0 L; 174.0 g/L; 343.6 g). The solution was concentrated and a second portion of the cyclic sulfite in dichloromethane (2.0 L; 155.9 g/L; 311.8 g) was added and further concentrated to approx. 2.3 L by distillation under atmospheric pressure. Toluene (1.7 L) was added to the batch and the distillation was continued to a final volume of approx. 1.7 L. Dimethylformamide (1.81 L) was added to the solution and concentration was continued under vacuum (approx. 105 Torr).

A 12 L 3 neck flask equipped with an overhead stirrer, a thermocouple, a distillation head and a nitrogen inlet which contained 2.2 L of the above solution of cyclic sulfite (655.3, 4.40 mol) in DMF:toluene (97:3/v:v) at room temperature was charged with sodium cyanide (218.9 g;. 4.40 mol) and sodium iodide (131.9 g; 0.88 mol). The reaction mixture was heated to 70°±3° C. over a 1 h period and aged at that temperature until the reaction was complete.

The reaction mixture was slowly diluted with 6.6 L of toluene maintaining the temperature of the batch at approx. 70° C. The hazy amber solution was charged with 80 mL of water over a 30 min period. The reaction mixture was cooled to 27° C. and the reaction flask was equipped with a 2 L dropping funnel which contained 2 L of toluene. The reaction mixture was concentrated under vacuum while the toluene was added from the dropping funnel. The reaction mixture was cooled overnight and then filtered through a medium porous sintered glass funnel (3 L); the cake was then flushed with an additional 2.2 L of toluene. The yield of the title compound was 87.5%.

EXAMPLE 3

1-(Acetylthiomethyl)cyclopropaneacetonitrile

Method A

A 500 mL round bottom flask equipped with an overhead stirrer, a thermocouple, distillation head and receiving flask was charged with the solution of the hydroxy-nitrile of Example 2 in isopropyl acetate and DMF (118 mL; 91 mg/mL; 10.74 g). The solution was concentrated to approx. 50 mL by distillation under atmospheric pressure. Isopropyl acetate (200 mL) was added to the batch and the distillation was continued to a final volume of 154 mL.

The distillation set up was replaced with an addition funnel. The solution was cooled to −3°±2° C. and triethylamine (17.4 mL) was added over 1 minute. Mesyl chloride (8.93 mL) was added slowly from the addition funnel keeping the temperature of the batch below 0° C. The addition took 30 minutes. The reaction mixture (approx. 180 mL) was transferred to a separatory funnel containing cold (0°–5° C.) water (76 mL). After equilibration, the layers were separated and the organic layer was washed with brine (76 mL).

The solution of 1-(methanesulfonyloxymethyl)cyclo-propane-acetonitrile was transferred to a 500 mL round bottom flask equipped with an overhead stirrer, a thermocouple and a nitrogen inlet. Solid potassium thioacetate (14.28 g) was added to the solution at 0° C. The heterogeneous mixture was warmed to 20°±2° C. and aged for 16 to 18 hours. Water (76 mL) was added to the reaction mixture and the contents of the reaction flask were transferred to a separatory funnel. The layers were separated and the organic layer was washed with brine (76 mL). The solution of the title compound in isopropyl acetate was concentrated under vacuum (75 Torr, 50° C.) to a volume of approx. 50 mL. Toluene (3×75 mL) was added and the concentration was continued under vacuum (60 Torr, 50° C.) until <1% of isopropyl acetate remained. Assayed yield of title compound=13.12 g (81%).
Method B.

A solution of 1-(hydroxymethyl)cyclopropaneacetonitrile (34.2 g, 0.308 mol) in toluene:DMF (1.9:1,210 mL) and triethylamine (49.4 mL, 0.354 mol) were combined in a 3-neck, 1L round bottom flask equipped with mechanical stirring and a thermocouple, flushed with nitrogen and cooled to −15° C. Mesyl chloride (26 mL) was added dropwise over 0.5 hr., keeping the temperature below 5° C. Ethanol (77 mL), triethylamine (86 mL, 0.616 mol) and thiolacetic acid (26.4 mL) were added sequentially as quickly as possible. The mixture was removed from the cooling bath and heated to 35° C. This temperature was maintained until <1% mesylate remains, about 7 hrs. Water (250 mL) was added and the mixture was shaken. The phases were separated, the aqueous phase was back-extracted with toluene (200 mL), and the organic phases were combined to provide the title compound (48.3 g at 103 mg/mL, 93% yield, purity: 91 area %).

EXAMPLE 4

1-(Mercaptomethyl)cyclopropaneacetic acid

A 1 liter round bottom flask equipped with an overhead stirrer, a thermocouple, distillation head and receiving flask was charged with the solution of 1-(acetylthiomethyl)cyclo-propane-acetonitrile in toluene (248.2 mL; 16.93 g; 100.0 mmol). The solution was concentrated under vacuum (75 Torr, 50° C.) to a volume of approx. 100 mL. The distillation set up was removed, the solution was cooled under nitrogen to 20°–25° C., and aqueous 5N sodium hydroxide (100 mL; 500 mmol) was added. The biphasic mixture was vigorously agitated at 20°–25° C. for 16–18 hours.

The aqueous layer was transferred to a 250 mL flask equipped with an overhead stirrer, a thermocouple, a nitrogen inlet and a reflux condenser. The solution was refluxed for approx. 2 hours, cooled to 0°–5° C. and 8N hydrochloric acid (62.5 mL; 500 mmol) was added to adjust the pH of the aqueous medium to 2.0. Toluene (190 mL) was added to the aqueous slurry with good stirring. The biphasic mixture was transferred to a separatory funnel and the layers were separated. Toluene (100 mL) was added to the aqueous layer and the layers were separated. The two organic layers were combined and concentrated under vacuum (60 Torr, 50° C.) to 82 mL, and the concentrated solution was filtered. Assayed yield of title compound=11.99 g (82%). The solution of the title compound in toluene was stored under nitrogen.

A 250 mL round bottom flask equipped with an overhead stirrer, a thermocouple, distillation head and receiving flask was charged with the solution of the title compound in toluene (100 mL; 11.50 g; 78.66 mmol). The solution was concentrated under vacuum (45 Torr, ≦40° C.) to a volume of approx. 23 mL. Hexane (92 mL) was added to the solution at 20°±2° C., and the solution was seeded with 10 mg of the title compound. The mixture was aged at 20°±2° C. for approx. 2 hrs to obtain a good seed bed. A sample of the slurry was examined by cross-polarized microscopy to confirm crystallinity of the solid.

The slurry was cooled to 0° to −5° C. and aged for about 2 hours, then allowed to warm to 20°±2° C. and aged overnight to digest the fine crystals. The slurry was cooled to −20°±5° C. over 3 hours and aged for one hour. A sample of the slurry was examined by cross-polarized microscopy to confirm crystallinity of the solid. The slurry was filtered and the cake was washed with cold (20°±5° C.) hexanes (25 mL), then dried under suction under nitrogen at 20°±2° C.

$^1$H NMR (CDCl$_3$) δ11.8 (bs, 1H), 2.64 (d, 2H), 2.52 (s, 2H), 1.36 (t, 1H), 0.64–0.52 (m, 4H).

DSC melting endotherm with a peak temperature of 49° C. and an associated heat of 122 J/g.
X-ray powder diffraction*-crystallinity.

*X-ray powder diffraction patterns in this and subsequent Examples were obtained with APD3720 (Philips) instrument at ambient temperature and under N$_2$.

EXAMPLE 5

2-(2-(3(S)-(3-(2-(7-chloro-2-quinolinyl)-ethenyl)phenyl)-3-hydroxypropyl)phenyl)-2-propanol Step 1:

In a 5 L flask fitted with mechanical stirrer and distillation head, a suspension of methyl 2-(3(S)-(3-(2-(7-chloro-2-quinolinyl)ethenyl)phenyl)-3-hydroxypropyl)benzoate hydrate (EP 480,717, Example 146, Step 2) (300 g, 0.63 mol) in toluene (3250 mL) was heated to reflux. All solids dissolved to afford a yellow-orange solution. Toluene-H$_2$O azeotrope (250 mL) was removed by distillation at atmospheric pressure (temp. 84°–110° C., T=110° C. after approx. 200 mL was removed). The clear solution was cooled to 20° C. KF=76 μg/mL.

Step 2:

A 3-neck 12 L flask fitted with a mechanical stirrer and reflux condenser was charged with THF (2 L, anhyd.) and CeCl$_3$ (160 g, 0.65 mol, anhyd.). The gray suspension was heated at reflux for 3–5 hours, then the ivory white suspension was cooled to 0° C. A solution of MeMgCl$_1$ (3M in THF, 1100 mL, 3.30 mol) was added dropwise over 30 min to the CeCl$_3$ suspension, keeping T=0°±5° C. The solution was aged at 0° C. for 2 hours. The solution of hydroxy-ester in toluene obtained in is Step 1 was added dropwise over 1.5 h keeping $-1 \leq T \leq 5°$ C. The solution was aged for 0.5 h after addition was complete. The reaction was then quenched by cautious addition to 1:12M HOAc/toluene (5 L ea) keeping T≤25° C. The pale yellow solution was stirred at 20°–25° C. for 10 min, then the layers were separated. The organic layer was washed with 1×5 L 10% Na$_2$CO$_3$ followed by 1×5 L H$_2$O. The organic layer (33 mg/mL of the title compound) was concentrated by distillation in vacuo (100 mbar, 40° C.) to afford a yellow solution of the title compound (approx. 180–190 mg/mL).

Step 3.

A crude solution of the title compound (the diol) in THF/toluene was concentrated from a 23.5 mg diol/mL solution to 253 mg diol/mL by distillation at atmospheric pressure (T=84°–110° C.). The solution temperature was then lowered to and maintained at 50° C. Seeding at 50° C. resulted in solution of the diol seed. Hexanes (50 mL) were added dropwise over 1 hour and then the reaction was seeded again. Once again, the seed appeared to dissolve. An additional aliquot of hexanes (25 mL) was added in a dropwise manner over 15 minutes, at which point white solids began to appear in the crystallization vessel. The crystallization was aged for 10 minutes followed by the addition of hexanes (85 mL) over 30 min. The crystallization was aged at 50° C. for 30 minutes followed by the addition of hexanes (160 mL) in one portion. Following a 30 minute age, the reaction mixture was cooled to 25° C. over 60 min., and filtered. The title compound was isolated in 89 yield (99.0 analytical %, 99.6 wt % purity).

EXAMPLE 6

2-(2-(3(S)-(3-(2-(7-chloro-2-quinolinyl)-ethenyl)phenyl)-3-methanesulfonyloxypropyl)phenyl)-2-propanol A 100 L round bottom flask fitted with a mechanical stirrer, thermocouple, and addition funnel was purged with N$_2$. The flask was charged with a solution of the diol in toluene (product of Example 5, 17.7 L, 348.5 g/L), CH$_3$CN (45.4 L), and diisopropylethylamine (2720 mL). The solution was cooled to T=−25°±3° C. in a CO$_2$/methanol bath. Methanesulfonyl chloride (1140 mL) was added dropwise over 2.5 h, keeping the T=−25°±2° C. After the addition of mesyl chloride the reaction mixture was seeded with granular seed of the title compound (5.0 g) and aged at −25° C. for 2 hours to afford a thin slurry (large cubic crystals by microscopy; supernatant assay: 21 g/L mesylate; subsequent experiment yielded needle crystals). The temperature was reduced to −35° C. over 1 hour and then aged for 1 hour (supernatant assay: 14 g/L mesylate). The product was isolated by filtration of the cold suspension under a blanket of N$_2$. The filter cake was washed with cold CH$_3$CN (14 L, −30° C.), followed by a cold hexane wash (16 L, 5° C.). After the washes, the cake was dried on the filter by pulling N$_2$ through the cake at 5° C. for 20 hours. The cake was packaged at 5° C. in double polypropylene bags in a fiber drum and stored at −18° C. to afford the product as a pale yellow solid (5844 g corrected for wt % purity, 81% yield).

$^1$H NMR (CDCl$_3$) δ8.11 (m, 2H), 7.69 (m, 5H), 7.41 (m, 5H), 7.19 (m, 3H), 5.70 (dd, 1H), 3.25 (m, 1H), 3.04 (m, 1H), 2.76 (s, 3H), 2.45 (m, 1H), 1.92 (s 1H), 1.65 (s, 6H).

X-ray diffraction pattern: as shown in FIG. 1. needle form instead of cubic.

EXAMPLE 7

1-(((1(R)-(3-(2-(7-chloro-2-quinolinyl)ethenyl)-phenyl)-3-(2-(1-hydroxy-1-methylethyl)phenyl)propyl)thio)methyl)-cyclopropaneacetic acid dicyclohexylamine salt Step 1:

To a 100 L reactor equipped with a mechanical stirrer, a thermocouple, a nitrogen inlet and an addition funnel were placed tetrahydrofuran (33 L) and 1-(mercaptomethyl)cyclopropaneacetic acid (1.317 kg, 7.938 mol). The mixture was stirred for 10 minutes to ensure complete dissolution. A clear, pale yellow solution resulted. The solution was cooled to −15°±2° C. and n-butyl lithium (1.56M in hexanes, 10.5 L, 16.38 mol) was added over 75 minutes, maintaining the temperature of the reaction mixture <−5° C. The slurry was aged at −5°±2° C. for 30 minutes.

Step 2:

To a 50 L flask equipped with a stirrer, a thermocouple and a nitrogen inlet was placed tetrahydrofuran (20 L). The solvent was cooled to 0°–5° C. The mesylate of Example 6 (4.501 kg, 7.558 mol) was added via a powder funnel and tetrahydrofuran (2.5 L) was used to rinse the funnel. The mixture was stirred for 15 minutes to ensure complete dissolution. A clear, pale yellow solution resulted.

Step 3:

The solution of the mesylate from Step 2 was transferred using a 0.25" o.d. polypropylene tubing under nitrogen pressure to the dianion slurry of Step 1 at −5°±2° C. over 75 minutes. The reaction solution was aged at −5°±2° C. for 8.5 hours. The reaction was quenched by pouring the clear, yellow reaction solution into a mixture of ethyl acetate (55 L) and 10% sodium chloride solution (55 L). The mixture was agitated for about 30 minutes and then the layers were allowed to separate. Two clear layers were obtained. The aqueous waste layer was drained off. The organic product layer was washed with 0.5M tartaric acid (36 L), then twice with water (36 L each time). The product solution was concentrated under vacuum to approx. 10 L. The product was dissolved in ethyl acetate (44 L) and the solution was allowed to equilibrate to room temperature (20°±2° C.).

Step 4:

To the solution of the free acid in ethyl acetate (54 L) in 2×100 L, 3necked flask equipped with a mechanical stirrer, a thermocouple, a nitrogen inlet and an addition funnel was added dicyclohexylamine (1.8 L). The clear solution was seeded with the dicyclohexylamine salt of the title compound (14 g). The resulting mixture was aged for about an hour, by which time a thick slurry resulted. A sample of the slurry was examined by cross-polarized microscopy to confirm crystallinity of the solid. Hexane (108 L) was slowly added over 2 hours maintaining a good agitation of the slurry. The slurry was aged at 20°±2° C. overnight. A sample of the slurry was examined by cross-polarized microscopy to confirm crystallinity of the solid. The slurry was suction filtered and the cake washed with cold (0°±2° C.) 1:2 ethyl acetate:hexanes (32 L). The product was dried under vacuum at 40°±2° C. with a nitrogen purge.

Isolated yield=4.745 kg (99 A %; 96 wt %; >99.8% ee; 79% yield).

¹H NMR (CD₃OD) δ8.25 (d, 1H), 7.95 (d, 1H), 7.86 (d, 1H), 7.83 (d, 1H), 7.77 (d, 1H), 7.70 (bs, 1H), 7.54 (d, 1H), 7.49 (d, 1H), 7.46–7.35 (m, 4H), 7.12–7.03 (m, 3H), 4.87 (s, active H), 4.03 (dd, 1H), 3.11–3.05 (m, 3H), 2.84–2.81 (m, 1H), 2.64 (d, 1H), 2.52 (d, 1H), 2.38 (d, 1H), 2.29 (d, 1H), 2.23 (m, 1H), 2.00 (m, 4H), 1.82 (m, 4H), 1.66 (m, 2H), 1.51 (two s, 6H), 1.37–1.14 (m, 10H), 0.53–0.32 (m, 4H).

X-ray powder diffraction pattern: as shown in FIG. 2.

EXAMPLE 8

Sodium 1-(((1(R)-(3-(2-(7-chloro-2-quinolinyl)ethenyl)-phenyl)-3-(2-(1-hydroxy-1-methylethyl)phenyl)propyl)thio)methyl)cyclopropaneacetate Toluene (1000 mL) and water ((950 mL) were placed in a 12 liter extractor equipped with an overhead stirrer, a thermocouple, a nitrogen inlet and an addition funnel. With good mixing of the solvents, solid dicyclohexylamine salt of Example 7 (64.3 g, 82.16 mmol) was added via a powder funnel and toluene (260 mL) was used to rinse in the remaining solid. To the well stirred suspension, acetic acid (2M, 62 mL, 124 mmol) was added at room temperature. After approximately 10 minutes stirring was stopped. Two clear phases (yellow organic layer and colorless aqueous layer) resulted, and the aqueous waste layer was drained off. Water (950 mL) was charged to the extractor and the layers were mixed thoroughly for approx. 10 minutes. The agitation was stopped and the aqueous waste layer was drained off.

To the organic layer (1270 mL) containing the free acid a titrated solution of sodium hydroxide in 1% aqueous ethanol (aqueous without ethanol (0.486M, 169 mL, 82.13 mmol) was added in a steady stream over 10 minutes at room temperature under a nitrogen atmosphere. After 10 minutes age, the clear solution of the desired sodium salt was filtered through a pad of solkafloc using toluene (100 ml) for transfer and cake wash.

The clear tiltrate was transferred under nitrogen to a 3 liter, 3-necked flask equipped with an overhead stirrer, a thermocouple, a nitrogen inlet and a distillation head. The solution was concentrated under vacuum to about 400 ml (ca. 40 mm Hg, ≦40° C.). The distillation head was replaced with a reflux condenser and an addition funnel. The concentrate was maintained at 40°±2° C. and acetonitrile (400 mL) was added over 20 minutes. The clear solution was seeded with 0.5 g of the crystalline sodium salt, and the resulting mixture was maintained at 40°±2° C. for 1.5 hours, by which time a good seed bed was established.

Acetonitrile (400 ml) was slowly added over 20 minutes, maintaining the batch temperature at 40°±2° C. The white suspension was stirred at 40°±2° C. for 1 hour and acetonitrile (400 mL) was slowly added over 20 minutes. The slurry was aged at 40°±2° C. for 12 hours. A sample of the suspension was examined by cross-polarized microscopy to confirm crystallinity of the solid. The suspension was cooled to RT and aged at RT for 1 hour. The crystalline sodium salt was suction filtered through a sintered funnel under nitrogen. The cake was washed with acetonitrile (400 ml). The crystalline sodium salt cake was broken up in a nitrogen glove bag and dried under vacuum with nitrogen bleed at 40–45° C. The product (49 g, 80.59 mmol, 98% yield) was packaged in a well sealed brown bottle under nitrogen. The reaction mixture and the isolated product were protected from light at all times.

HPLC assay of the sodium salt: >99.5 A %. Chiral purity: 99.8% ee.

¹H NMR (CD₃OD) δ8.23 (d, 1H), 7.95 (d, 1H), 7.83 (d, 1H), 7.82 (d, 1H), 7.75 (d, H), 7.70 (bs, 1H), 7.54 (dt, 1H), 7.46 (dd, 1H), 7.42–7.35 (m, 3H), 7.37 (d, 1H), 7.14–7.00 (m, 3H), 4.86 (s, active H), 4.03 (dd, 1H), 3.09 (m, 1H), 2.82 (m, 1H), 2.66 (d, 1H), 2.52 (d, 1H), 2.40 (d, 1H), 2.30 (d, 1H), 2.24–2.14 (m, 2H), 1.51 (two s, 6H), 0.52–0.32 (m, 4H).

DSC melting endotherm with a peak temperature of 133° C. and an associated heat of 25 J/g.

Figure 3:
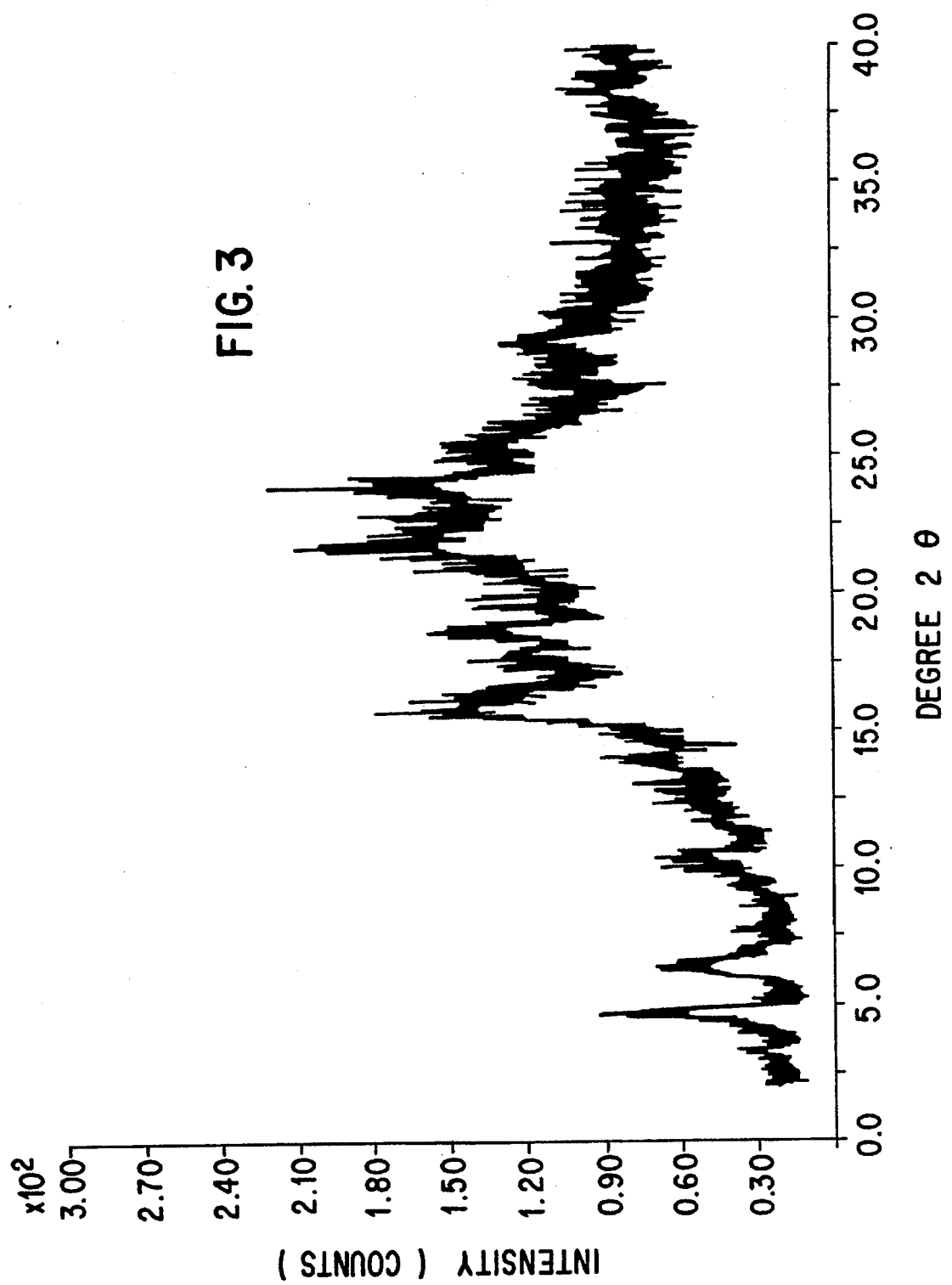
FIG. 3 depicts the X-ray powder diffraction pattern of the compound of Example 8.

X-ray powder diffraction pattern: as shown in FIG. 3.

EXAMPLE 9

2-(2-(3(S)-(3-(2-(6,7-difluoro-2-quinolinyl)-ethenyl)phenyl)-3-methanesulfonyloxypropyl)phenyl)-2-propanol The general procedures described in Examples 5 and 6 were followed except methyl 2-(2-(3(S)-(3-(2-(6,7-difluoro-2-quinolinyl)-ethenyl)phenyl)-3-hydroxypropyl)benzoate was used, in Example 5, Step 1, about 750 mL to about 1 L of the toluene-H₂O azeotrope was removed, and in Example 6 DMF:acetonitrile (3: 1) was used as the solvents to provide the title compound.

EXAMPLE 10

Figure 4:
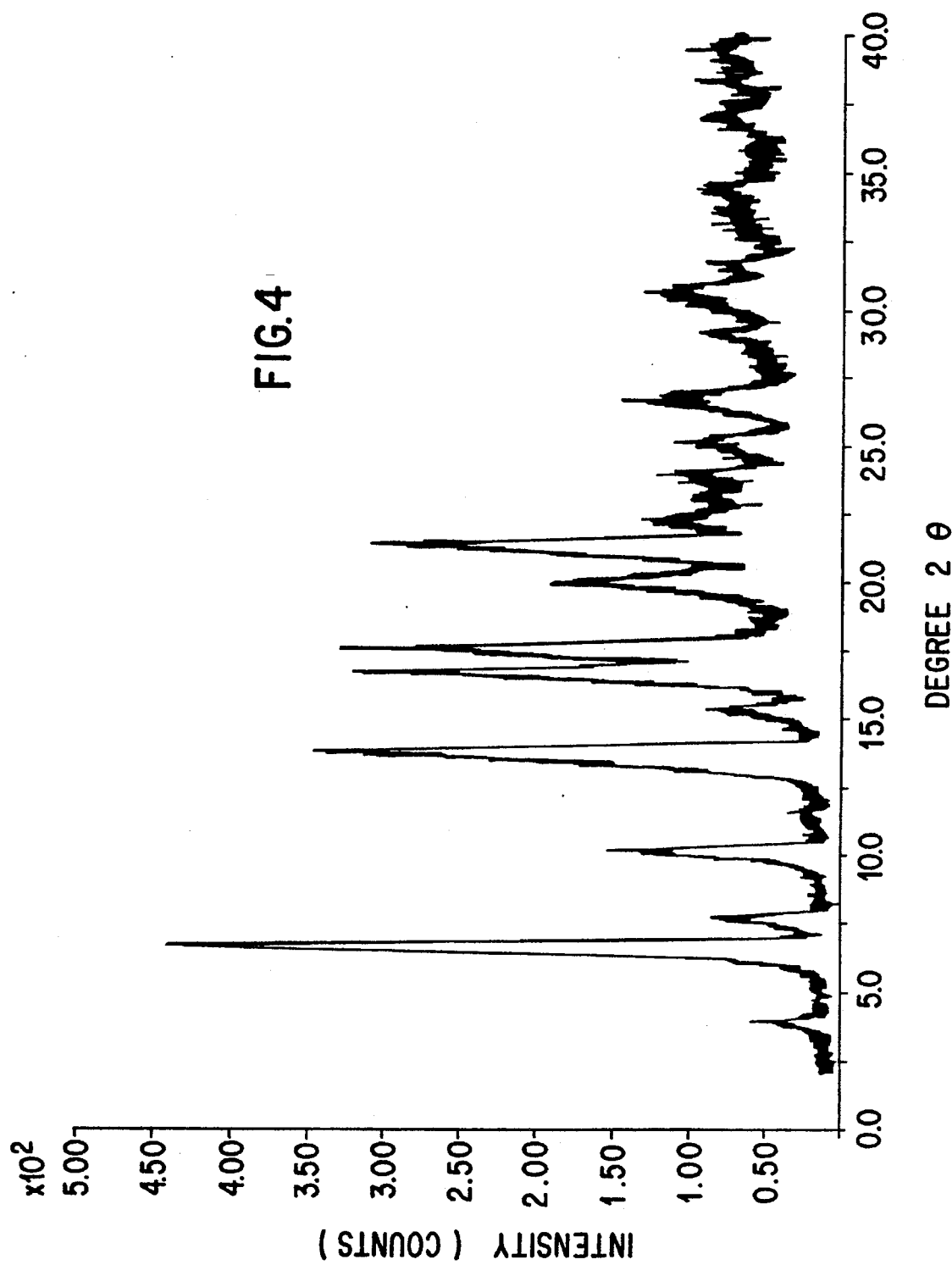
FIG. 4 depicts the X-ray powder diffraction pattern of the compound of Example 10.

1-(((1(R)-(3-(2-(6,7-difluoro-2-quinolinyl)ethenyl)-phenyl)-3-(2-(1-hydroxy-1-methylethyl)phenyl)propyl)thio)methyl)-cyclopropaneacetic acid dicyclohexylamine salt The general procedure of Example 7 was followed except the compound of Example 9 was used to provide the title compound. DSC melting endotherm with a peak temperature of 132° C. X-ray powder diffraction pattern: as shown in FIG. 4.

EXAMPLE 11

Figure 5:
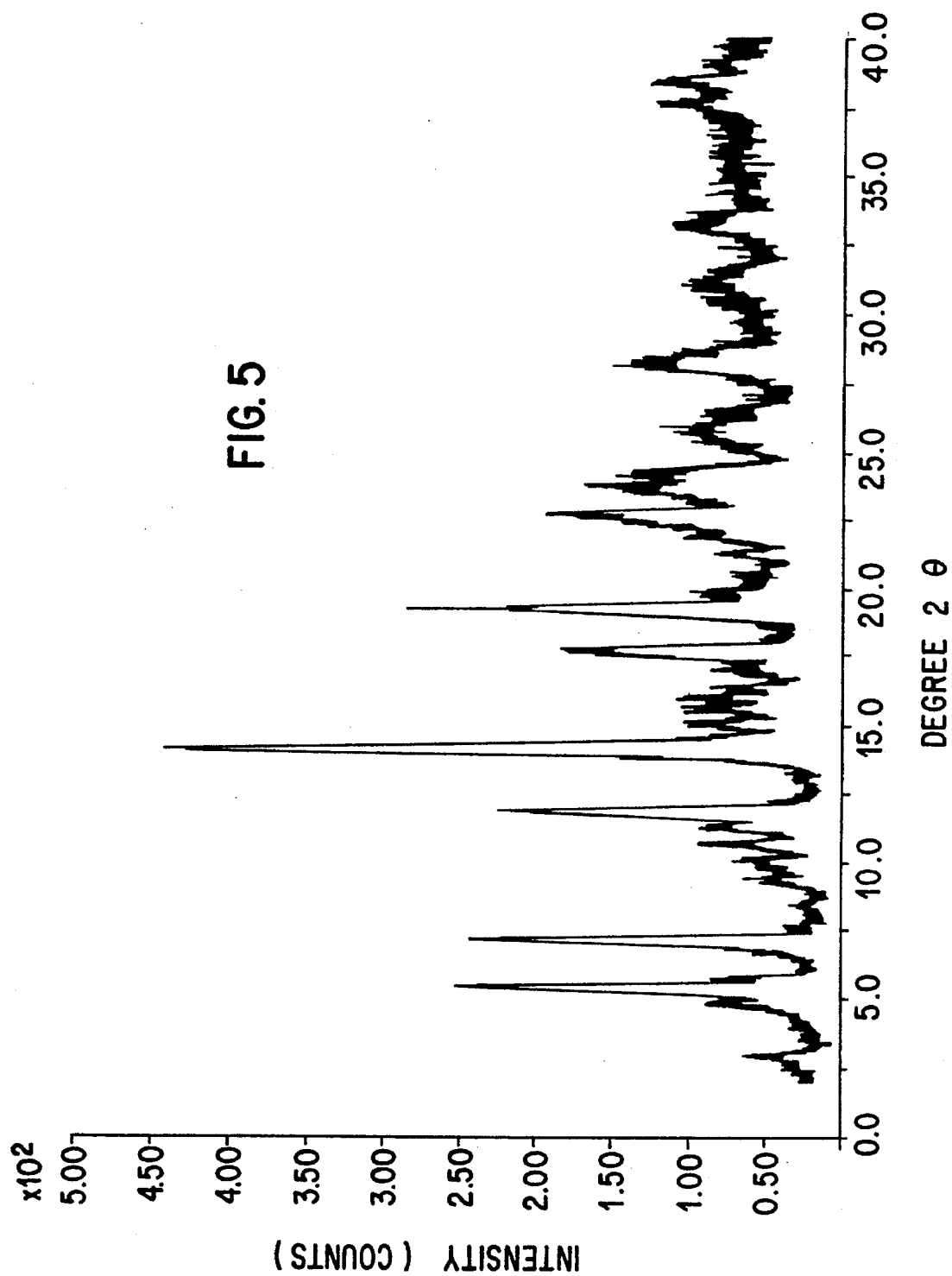
FIG. 5 depicts the X-ray powder diffraction pattern of the compound of Example 11.

Sodium 1-(((1(R)-(3-(2-(6,7-difluoro-2-quinolinyl)ethenyl)-phenyl)-3-(2-(1-hydroxy-1-methylethyl)phenyl)propyl)thio)methyl)-cyclopropaneacetate The general procedure of Example 8 was followed except the compound of Example 10 was used to provide the title compound. DSC endotherm with a peak temperature of 119° C. X-ray powder diffraction pattern: as shown in FIG. 5.

EXAMPLE 12

Alternative method for the preparation of 1-(mercaptomethyl)cyclopropaneacetic acid Step 1:

Diisopropyl sulfite

Toluene (500 mL) and isopropanol (306 mL, 4 mole) were combined under nitrogen in a 2L flask equipped with a dropping funnel and thermocouple. Thionyl chloride (73 mL, 1 mole) was added from the dropping funnel over 30 minutes maintaining the temperature at 15°–25° C. When the addition was complete, the reaction mixture was put under vacuum to remove HCl. Vigorous HCl evolution was noted at 150 mm.

The pressure was lowered slowly. When gas evolution ceased, the mixture was concentrated to remove toluene and excess isopropanol. Concentration was continued until less than 1% isopropanol remained. Yield=159 g, 95%. Triethylamine (1 mL) was added to stabilize the product and the incipient precipitate was filtered away. The solution was used as is.

Step 2:

1-(Hydroxymethyl)cyclopropaneacetonitrile

Dimethylformamide (225 mL) and 1,1-cyclopropanedimethanol (26.6 g; at 95 wt %, actual amount=25.5 g, 250 mmol) were placed in a 1L flask equipped with a vacuum distillation apparatus. DMF (25 ml) was distilled at 75° C./50 torr, and to the remaining solution was added a solution of diisopropyl sulfite in toluene (81.6 mL, 49.9 g, 300 mmol). Toluene (50 mL) was distilled at 52° C./55 torr, and the resulting solution had a KF of 98 μg/mL.

Sodium t-butoxide, (2M in tetrahydrofuran, 2.0 mL) was added, and distillation was begun again at 45° C./50 torr, with 30 mL of distillate collected. Distillation was continued to collect 60 mL at 50°–70° C./50 torr. Sodium t-butoxide (1.0 mL) was added and the distillation was continued to collect 60 mL of distillate at 60°–75° C./50 torr. After the addition of more sodium tobutoxide (0.5 mL), and distillation of 30 mL at 70–75° C./50 torr, the distillation was stopped, and the mixture was maintained at 70° C. for 1 h and then cooled to room temperature. The yield of 1,1-cyclopropanedimethanol cyclic sulfite=33.0 g, 89%).

Sodium cyanide (13.5 g, 275 mmol) and sodium iodide (7.5 g, 50 mmol) were added to the solution obtained above, and the heterogeneous mixture was slowly warmed over 1 h to 70° C., and aged for about 40 h with vigorous stirring. Toluene (400 mL) was added slowly at 70° C., and then water (6 mL) was added dropwise over 30 minutes. The mixture was then dried by vacuum distilling 100 mL of toluene; when the KF of the mixture was 200 μg/mL, it was cooled to 10° C. and filtered. The precipitate was washed with toluene (100 mL), and the combined filtrate contained 21.4 g of the title compound (77% from 1,1-cyclopropyldimethanol).

Step 3:

1-(Acetylthiomethyl)cyclopropaneacetonitrile

The product of Step 2 in toluene/DMF (1.9:1) (210 mL for 34.2 g of the product compound) and triethylamine (49.4 mL, 0.354 mol) were combined in a 3-neck 1L round bottom flask equipped with mechanical stirring and a thermocouple, flushed with nitrogen and cooled to −15° C. Mesyl chloride (26 mL, 0.339 mmol) was added dropwise over 0.5 h, keeping the temperature below ±5° C.

Triethylamine (86 mL, 0.616 mmol) and thiolacetic acid (26.4 mL, 0.40 mole) were added sequentially as quickly as possible; the mixture was removed from the cooling bath and heated to 35° C. This temperature was maintained until >1% of the mesylate remained (about 7 h). Water (250 mL) was added, the mixture was shaken, and the two phases were separated. The aqueous phase was extracted with toluene (200 mL), and the organic phases were combined. The combined organic phases (470 mL) contained 48.3 g (93%) of the desired product.

Step 4:

1-(Mercaptomethyl)cyclopropaneacetic acid

The product solution of Step 3 (447 g containing 48 g of the product compound) was washed with deionized water (2×150 mL). In a 1L three-neck flask equipped with nitrogen inlet and mechanical stirring, the organic layer was deoxygenated. Deoxygenated 5N NaOH (284 mL) was added. The mixture was vigorously stirred at ambient temperature for 6–10 h until 2% starting material remained. The aqueous layer was separated and heated at 80° C. for 12–16 h until none of the intermediate 1-(mercaptomethyl)cyclopropaneacetamide remained.

The reaction was cooled to 25–30° C. and 930 mL of deoxygenated heptane was added. The mixture was acidified to pH 3.5–4.0 with 5M NaHSO$_4$ solution over 1 h with stirring and allowed to warm to 30° C. The layers were separated at 30° C. and the aqueous layer was backextracted with 310 mL heptane. The combined organic layers were concentrated to 180 mL.

The mixture was warmed to 34° C. to completely solubilize the product and then allowed to slowly cool to 25° C. over 1 h. The mixture was seeded at 30° C. After stirring at 25° C. for 1 h to ensure a good seed bed, the mixture was cooled to −5° C. over 3 h. After stirring at −5° C. for 30 minutes, the mixture was filtered and washed with 20 mL of cold heptane. The title compound was obtained as an off-white crystalline solid (34.3 g, 83%).

EXAMPLE 13

1-(((1(R)-(3-(2-(7-chloro-2-quinolinyl)ethenyl)-phenyl)-3-(2-(1-hydroxy-1-methylethyl)phenyl)propyl)thio)methyl)cyclopropaneacetic acid dicyclohexylamine salt crystallized from toluene/heptane Step 1:

To a 2.0 L reactor equipped with a mechanical stirrer, a thermocouple, a nitrogen inlet and an addition funnel were placed tetrahydrofuran (132 ml) and 1-(mercaptomethyl)cyclopropaneacetic acid (9.830 g, 65.98 mmol). The mixture was stirred for 10 minutes to ensure complete dissolution. A clear, pale yellow solution resulted.

The solution was cooled to −15°±2° C. n-Butyl lithium (1.70M in hexanes, 79.6 ml, 135.26 mmol) was added over 30 minutes, maintaining the temperature of the reaction mixture <−5° C. The slurry was aged at −5°±2° C. for 30 minutes.

Step 2:

To a 250 ml flask, equipped with a stirrer, a thermocouple and a nitrogen inlet were placed mesylate of Example 6 (36.52 g, 62.68 mmol) and THF (106 ml). The solution was cooled to 0°–5° C. The mixture was stirred for 15 minutes to ensure complete dissolution. A clear, pale yellow solution resulted.

Step 3:

The solution of the mesylate of Step 2 was transferred via cannula to the dianion slurry of Step 1 at −5°±2° C. over 5 minutes. The reaction solution was aged at 0°±2° C. for 15 hours. The heterogeneous, yellow reaction solution was quenched by addition to a solution of 10% brine (200 ml). The mixture was agitated for about 10 minutes and the layers were allowed to separate. The organic product layer was washed with 0.5M tartaric acid (280 ml), then washed with water (2×120 ml).

The product solution was transferred to a 500 ml 1-neck flask. To this solution 250 ml of toluene was added along with s dicyclohexylamine (14.44 ml, 72.60 mmol). This clear solution was treated with Darco G-60 (1.8 g) and the mixture was stirred under nitrogen for an hour. The mixture was filtered through a bed of solka floc (12 g) using toluene (20 mL) for rinse and transfer. The filtrate and wash were combined and concentrated under vacuum to ~200 ml. Another 200 ml of toluene was then added and the volume was reduced to 200 ml again.

The above solution was diluted to 640 ml with toluene and transferred to a 2.0 L, 3-necked flask equipped with a mechanical stirrer, a thermocouple, a nitrogen inlet, and an addition funnel. The clear solution was seeded with dicyclohexylamine salt of the title compound (200 mg) previously crystallized from toluene/heptane. The resulting mixture was aged for about 3 hours, by which time a thick slurry resulted. A sample of the slurry was examined by cross-polarized microscopy to confirm crystallinity of the solid. Heptane (280 ml) was slowly added over 2 hours maintaining a good agitation of the slurry. The slurry was aged at 20°±2° C. overnight. A sample of the slurry was examined by cross-polarized microscopy to confirm crystallinity of the solid. The slurry was suction filtered and the cake washed with 1:1 heptane:toluene (200 ml). The product was dried under vacuum at 40°±2° C. with a nitrogen purge. Isolated yield of the title dicyclohexylamine salt=40.39 g (purity: 99.3 A %, >99.8% ee; 80.6% yield).

In case the purity of the product is below about 99%, the product may be further purified by swishing with toluene/heptane. For example, the DCHA salt (98.6A % purity, 10.03 g) was swished with toluene/heptane (1.5:1, 300 ml) at room temperature for 5 hours. The slurry was filtered and dried as earlier to obtain further purified DCHA salt (9.63 g, 99.4 A %).

X-ray powder diffraction pattern: as shown in FIG. 6.

EXAMPLE 14

Alternative method for the preparation of sodium 1-(((1 (R)-(3-(2-(7-chloro-2-quinolinyl)ethenyl)phenyl)-3-(2-(1-hydroxy-1-methylethyl)phenyl)propyl)thio)methyl)cyclopropaneace To a 1L round bottom, 3 neck flask equipped with overhead stirrer and nitrogen bubbler were charged 285 ml of toluene, 85 ml THF, and 215 ml deionized water. To this was charged 25.0 grams of solid DCHA salt of 1-(((1-(R)-(3-(2-(7-chloro-2-quinolinyl)ethenyl)phenyl)-3-(2-(1-hydroxy-1-methylethyl)phenyl)propyl)thio)methyl)cyclopropaneacetic acid (97.3 wt % purity). To the resulting slurry was charged 23.3 ml of 2.04M aqueous acetic acid.

The flask was purged 3 times with nitrogen and vacuum and left with a nitrogen blanket. The two phase mixture was agitated for 15 minutes. The agitation was stopped and the mixture was transferred to a 1000 ml separatory funnel, the batch was settled for 15 minutes, and the aqueous layer was cut off.

The organic layer was washed with deionized water (2×215 mL) as above, and the organic layer was returned to a 1L round bottom flask and purged 3 times with nitrogen and vacuum. A 0.500M solution of NaOH in 1% aqueous ethanol (63.3 mL) was added to the organic layer. At the end of the addition one clear phase was present. The resulting solution was filtered through a 0.45 μm nylon membrane filter (precoated with 2.5 g of Solka Floc) into a second 1L round bottom flask. The funnel was rinsed with 50 ml of toluene which was combined with the initial filtrate. The resulting solution was vacuum distilled (T≦40° C.) to a volume of ~165 ml. Toluene (165 ml, 0.45 μm filtered) was added and the solution concentrated to 165 ml. The toluene dilution/concentration step was repeated to provide a solution of 165 ml final volume.

A slurry seedbed was prepared in a 1 liter resin kettle equipped with overhead stirrer and nitrogen bubbler. To the resin kettle were charged 32 ml of 0.45 μm filtered toluene, 64 ml of 0.45 μm filtered acetonitrile, and 3.86 g of title sodium salt seed.

The sodium salt concentrate (165 ml) and sieve dried, 0.45 μm filtered acetonitrile (330 ml, KF<100 μg/ml) were charged simultaneously to the seedbed over 8 hours via two syringe pumps. The seedbed temperature was maintained at 20° C. during the addition, and the flowrates were matched in order to maintain the crystallizer solvent ratio at ~2:1 acetonitrile:toluene. The microscopic appearance of the slurry and the supernatant concentration were monitored throughout the simultaneous addition. After the completion of the addition, the resulting slurry was aged overnight at 20° C. (16 hours).

The crystallized slurry was vacuum filtered under nitrogen insertion, leaving behind ~100 ml of slurry to serve as the seedbed for a subsequent crystallization. The filtered cake was washed with 238 ml of sieve dried, 0.45 μm filtered acetonitrile (KF<100 μg/ml). The resulting cake was dried in a vacuum oven at 40°–45° C. for 48 hours. A total of 17.75 g of sodium salt were recovered (99.3 wt %).

A second sodium salt formation and crystallization cycle was performed the same as described above, using the seedbed left from cycle #1. After the completion of the cycle #2 crystallization, the entire slurry was filtered without leaving behind a seedbed. The total product isolated from cycle #2 was 20.38 g (99.7 wt %). The overall material balance for the two cycles was 95.2%, with a yield of 92.1% (corrected for sampling the mechanical losses due to holdup in the crystallizer).

What is claimed is:

1. A process for the preparation of a compound of formula (I) or a sodium salt thereof

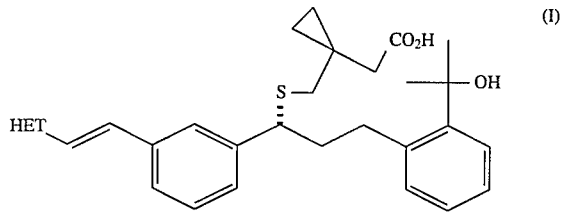

wherein HET is 7-chloroquinolin-2-yl or 6,7-difluoroquinolin-2-yl, which comprises:

generating the dilithium dianion of 1-(mercaptomethyl) cyclo-propaneacetic acid;

reacting said dianion with a compound of formula (II)

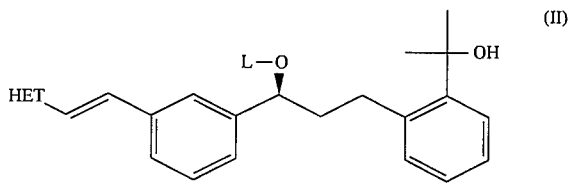

wherein HET is as defined above and L is arylsulfonyl or alkylsulfonyl.

2. A process according to claim 1 which further comprises: converting said compound of formula (I) in free acid form to the dicyclohexylamine salt.

3. A process according to claim 1 wherein HET is 7-chloroquinolin-2-yl, and L is methanesulfonyl.

4. A process according to claim 2 wherein HET is 7-chloroquinolin-2-yl, and L is methanesulfonyl.

5. A process for the preparation of the crystalline sodium salt of a compound of formula (I)

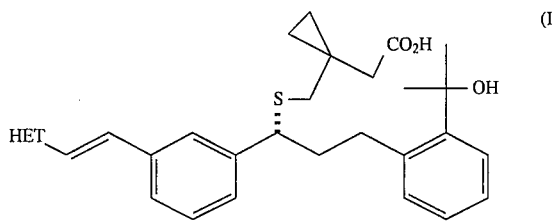

wherein HET is 7-chloroquinolino-2-yl or 6,7-difluoro-quinolin-2-yl, which comprises:

treating the dicyclohexylamine salt of a compound of formula (I) with an acid;

treating the product thus obtained with a source of sodium ion; and crystallizing the sodium salt.

6. A process of claim 5 wherein HET is 7-chloro-quinolin-2-yl.

7. A process of claim 6 wherein the crystallizing solvent is toluene:acetonitrile.

* * * * *